(12) United States Patent
Otsubo

(10) Patent No.: US 6,632,211 B2
(45) Date of Patent: Oct. 14, 2003

(54) DISPOSABLE DIAPER

(75) Inventor: Toshifumi Otsubo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/239,565

(22) Filed: Jan. 29, 1999

(65) Prior Publication Data

US 2001/0016720 A1 Aug. 23, 2001

(30) Foreign Application Priority Data

Jan. 30, 1998 (JP) .......................................... 10-019998

(51) Int. Cl.[7] .......................... A61F 13/15; A61F 13/20
(52) U.S. Cl. ........................ 604/385.22; 604/385.16; 604/385.26; 604/396; 604/400; 604/401
(58) Field of Search .............................. 604/385.1–402

(56) References Cited

U.S. PATENT DOCUMENTS

| | | | | |
|---|---|---|---|---|
| 1,118,643 A | * | 11/1914 | Emmers ..................... | 604/402 |
| 1,388,529 A | * | 8/1921 | Smith ........................ | 604/402 |
| 1,733,997 A | * | 10/1929 | Marr ......................... | 604/401 |
| 2,016,355 A | * | 10/1935 | Alsop ....................... | 604/397 |
| 2,545,099 A | * | 3/1951 | Mann ........................ | 604/400 |
| 2,823,676 A | * | 2/1958 | Clark ........................ | 604/401 |
| 3,688,767 A | * | 9/1972 | Goldstein ................... | 604/401 |
| 4,596,570 A | * | 6/1986 | Jackson et al. ............. | 604/387 |
| 4,834,738 A | * | 5/1989 | Kielpikowski et al. ..... | 604/385.2 |
| 4,892,598 A | * | 1/1990 | Stevens et al. ............ | 604/385.2 |
| 5,593,400 A | | 1/1997 | O'Leary | |
| 5,690,627 A | * | 11/1997 | Clear et al. ............... | 604/385.2 |
| 2002/0173764 A1 | * | 11/2002 | Takino et al. ............. | 604/385.28 |

FOREIGN PATENT DOCUMENTS

| | | | | |
|---|---|---|---|---|
| DE | 564904 | * | 11/1932 | .............. 604/385.1 |
| EP | 0006 01610 | * | 6/1994 | .............. 604/385.2 |
| EP | 0 761 194 | | 3/1997 | |
| EP | 0 763 353 | | 3/1997 | |
| EP | 0904753 A2 | * | 3/1999 | |
| GB | 2 284 741 | | 6/1995 | |
| JP | 3-122824 | | 12/1991 | |
| WO | WO 98/53785 | * | 12/1998 | ........... A61F/13/72 |

OTHER PUBLICATIONS

Copy of European Search Report, EP 99 30 0639, dated Oct. 10, 2000.

* cited by examiner

*Primary Examiner*—Karin Reichle
(74) *Attorney, Agent, or Firm*—Butzel Long

(57) ABSTRACT

A disposable diaper that includes a briefs-shaped cover member having an elastic stretchability in a vertical direction of the diaper, and an absorbent member that includes a topsheet and a backsheet both of which are not elastically stretchable at least in the vertical direction, and a liquid-absorbent core disposed therebetween. The absorbent member is suspended inside the cover member by suspender sheets that are elastically non-stretchable sheets, at least in the vertical direction, and have pleats which can be flattened out in a vertical direction of the diaper.

5 Claims, 4 Drawing Sheets

DISPOSABLE DIAPER

BACKGROUND OF THE INVENTION

This invention relates to a disposable diaper for absorbing and containing body exudates.

Japanese Utility Model Application Disclosure Gazette (Kokai) No. Hei3-122824 discloses an absorbent garment comprising a stretchable topsheet, a stretchable backsheet and a water-absorbent panel disposed between these two sheets, wherein the topsheet and the panel are bonded to each other at a plurality of dots.

However, this known garment is disadvantageous in that the topsheet has its intrinsic stretchability remarkably lessened in the region where it is bonded to the panel and can offer its intrinsic stretchability only in its region extending outwards beyond a peripheral edge of the panel. Consequently, the stretchability of the topsheet which can be utilized during practical use of the garment will be no more than the stretchability offered by an extremely limited portion of the topsheet in spite of intentionally using both the topsheet and the backsheet which are entirely stretchable. Generally, stretchable sheets are relatively expensive and therefore a noticeable cost performance can not be expected when a stretchable sheet is used in the manner of the above-mentioned prior art.

SUMMARY OF THE INVENTION

In view of the problem as has been mentioned above, it is an object of the invention to provide a disposable diaper which includes a cover having elastic stretchability in a vertical direction of the diaper.

According to the invention, there is provided a disposable diaper basically comprising a briefs-shaped cover member having a front waist region, a rear waist region and a crotch region extending between these two waist regions so as to form a waist-opening and a pair of leg-openings, and an absorbent element formed separately of the cover member. The absorbent element comprises a liquid-pervious topsheet, a liquid-impervious backsheet and a liquid-absorbent core disposed therebetween. The absorbent element extends longitudinally, i.e. vertically, on an inner side of the cover member from the crotch region into the front and rear waist regions.

The cover member is elastically stretchable in a vertical direction of the diaper. The absorbent element is not elastically stretchable at least in a vertical direction and is connected to an inner surface of the cover member in the proximity of the waist-opening in the front and rear waist regions by the suspender sheets which are not elastically stretchable at least in the vertical direction. The suspender sheets are respectively formed with pleats which extend circumferentially of the waist regions and can be flattened out in the vertical direction.

DESCRIPTION OF THE PREFERRED EMBODIMENTS

Details of a disposable diaper according to the invention will be more fully understood from the description given hereunder with reference to the accompanying drawings.

Figure 1:
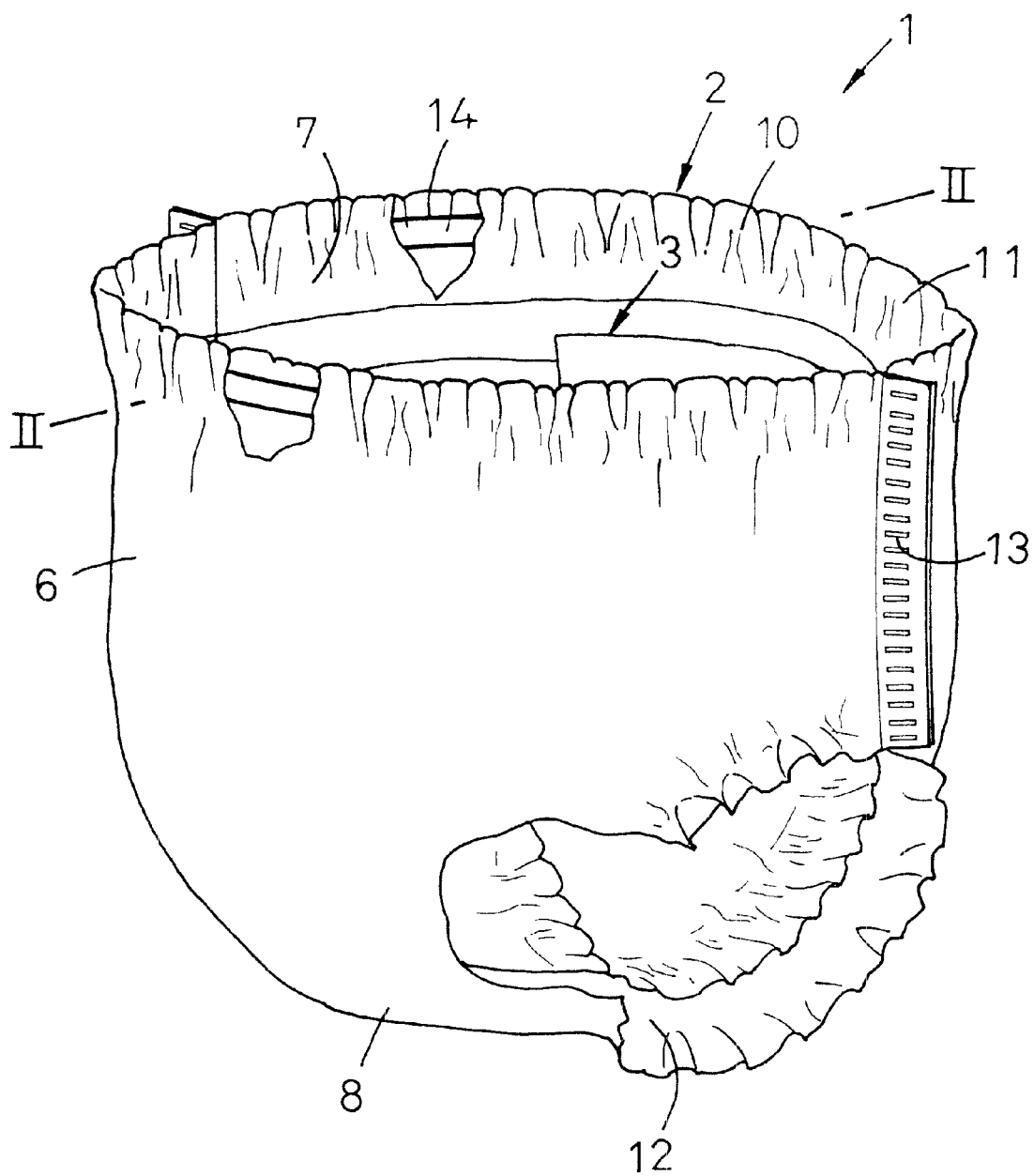
FIG. 1 is a perspective view showing a disposable diaper according to the invention as partially broken away.

Disposable diaper 1 shown by FIG. 1 in a perspective view as partially broken away generally consists of a briefs-shaped cover component 2 and an absorbent element 3 attached to an inner side of the cover member 2.

The cover member 2 comprises a front waist region 6, a rear waist region 7 and a crotch region 8 extending between these two waist regions 6, 7 so as to define a waist-opening 10 and a pair of leg-openings 12. The front and rear waist regions 6, 7 are placed flat together along their transversely opposite side edges and joined to each other at a plurality of joining zones 13 intermittently arranged in a vertical direction along each side edge. The waist-opening 10 is provided with an elastic member 14 extending circumferentially under appropriate tension.

Figure 2:
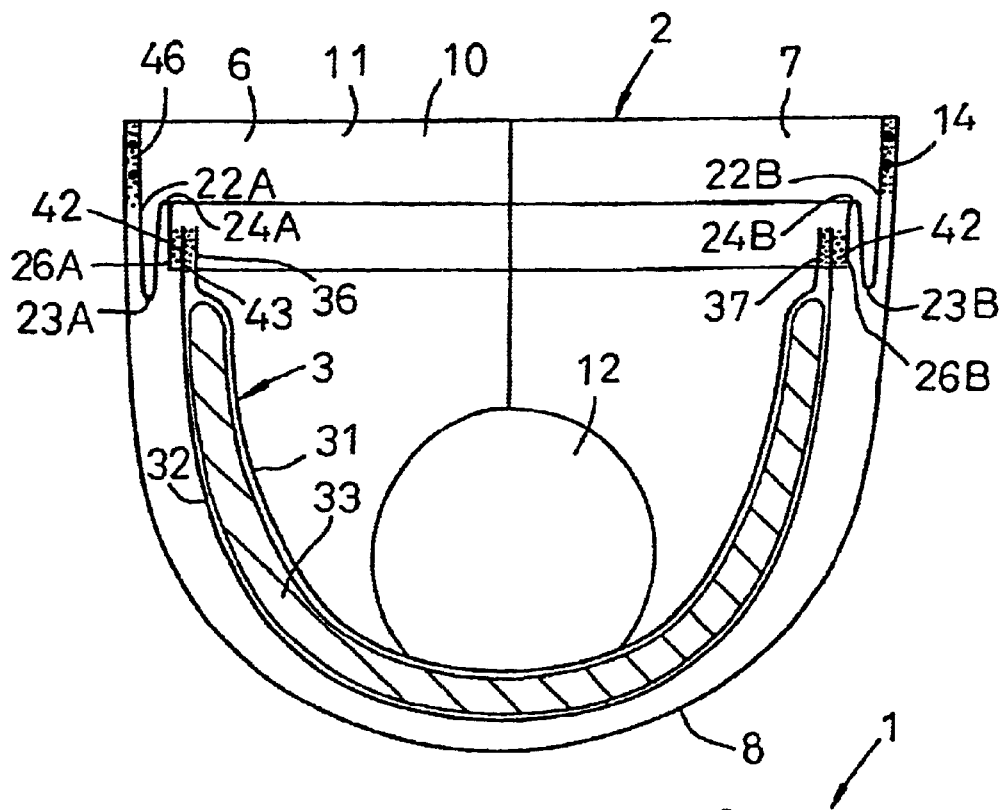
FIG. 2 is a sectional view taken along a line II—II in FIG. 1.
Figure 3:
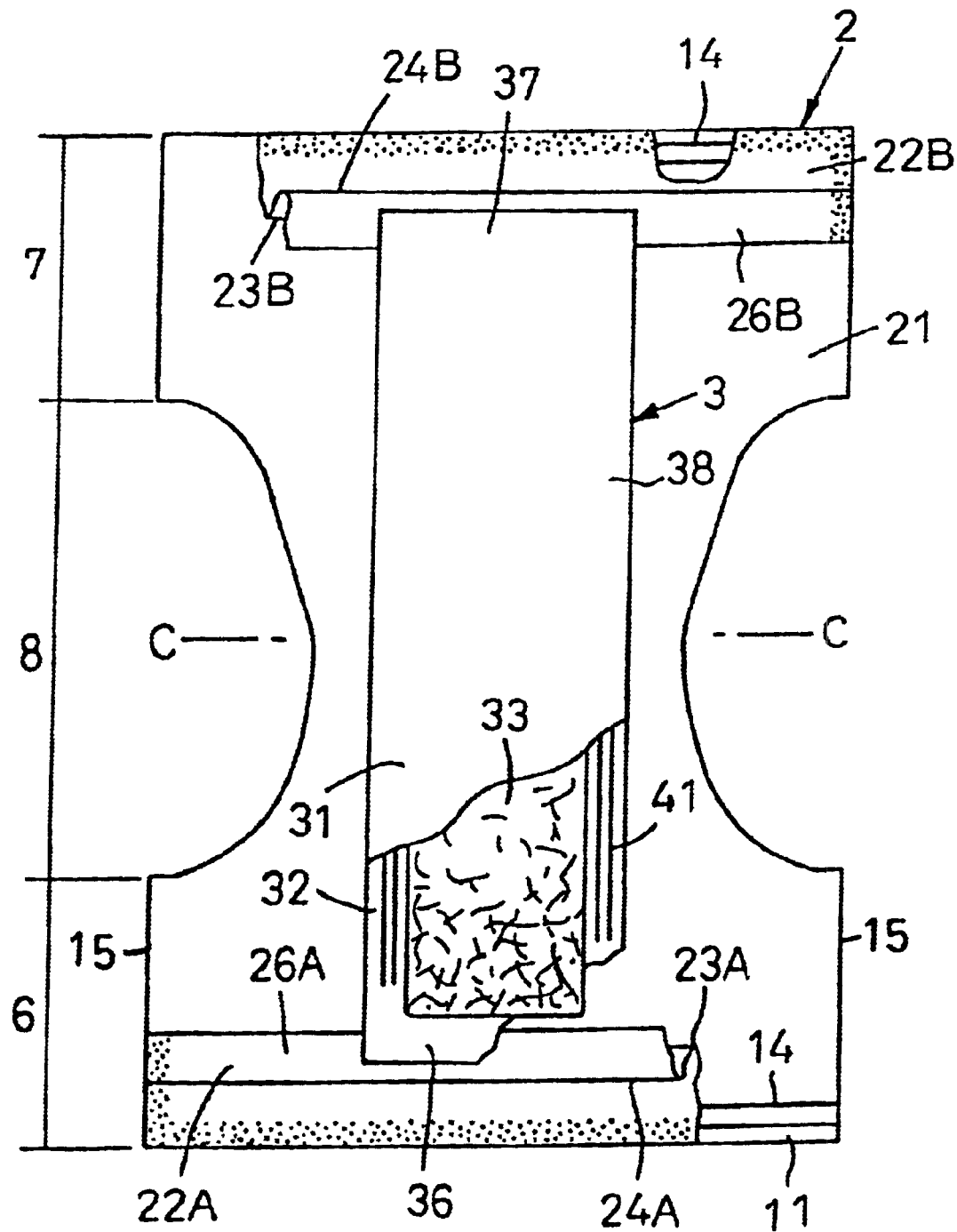
FIG. 3 is a plan view showing the diaper of FIG. 1 with front and rear waist regions separated from each other along their transversely opposite side edges and then flattened out with an inside of the diaper facing upwards, as partially broken away.

FIG. 2 is a sectional view taken along a line II—II in FIG. 1 and FIG. 3 is a plan view showing the diaper 1 of FIG. 1 with the front and rear waist regions 6, 7 separated from each other along the joining zones 13 and flattened out with an inside of the diaper 1 facing upwards, as partially broken away. The cover member 2 has an hourglass shape and is made basically of an elastic sheet 21 which is stretchable in a vertical direction of the diaper 1. The cover member 2 further includes a pair of suspender sheets 22A, 22B which are not elastically stretchable at least in a vertical direction of the diaper 1 and which are respectively attached to inner surfaces of the front and rear waist regions 6, 7 along peripheral edges of the waist-opening. Suspender sheets 22A, 22B extend in parallel to a center line C—C dividing a longitudinal dimension of the diaper 1 in two and are used to connect the absorbent component 3 to the cover component 2. The suspender sheets 22A, 22B are folded along first folding lines 23A, 23B lying relatively near the center line C—C and along second folding lines 24A, 24B lying relatively remote from the center line C—C to form pleats presenting Z- and inverted Z-shaped cross-sections, respectively. The suspender sheets 22A, 22B are joined to the inner surface of the cover member 2 along the peripheral edges 11 of the waist-opening 10 and the transversely opposite side edges 15 by means of hot melt adhesive 46 indicated by a plurality of dots so as to form relatively deformable pleats 26A, 26B on the sides of the suspender sheets 22A, 22B opposed to the center line C—C, respectively. The elastic member 14 extends circumferentially and is secured, under appropriate tension, to the inner surface of the cover member 2 along the peripheral edges 11 of the waist-opening 10 and is covered with the suspender sheets 22A, 22B. It is also possible to dimension these suspender sheets 22A, 22B so that they are narrower than a width of the diaper 1 and larger than a width of the absorbent element 3. In this case, the suspender sheets 22A, 22B may be joined to the cover member 2 along the peripheral edges 11 of the waist-opening 10 alone.

The absorbent element 3 has a rectangular shape larger in its longitudinal dimension than in its transverse direction as seen in FIG. 3 and comprises a liquid-pervious topsheet 31, a liquid-impervious backsheet 32 and a liquid-absorbent core 33 disposed between these two sheets 31, 32. The rectangular shape is defined by longitudinally opposite ends 36, 37 extending transversely of the cover member 2 and transversely opposite side edges 38, 39 extending longitudinally of the cover member 2. The topsheet 31 and the backsheet 32 which are not elastically stretchable at least in the vertical direction extend outwards beyond peripheral edges of the core 33 and are bonded to each other along such extensions by means of hot melt adhesive 43. The absorbent element 3 is provided along its transversely opposite side edges with elastically stretchable members 41, 41 longitudinally which extend between the topsheet 31 and the backsheet 32 and are secured to at least one of these sheets 31, 32. The longitudinally opposite ends 36, 37 of the absorbent element 3 have their outer surfaces bonded to the pleats 26A, 26B of the suspender sheets 22A, 22B on their inner surfaces, respectively, by means of hot melt adhesive 42. The core 33 is formed by fluff pulp fibers or a mixture of fluff pulp fibers and superabsorptive polymer particles and is not elastically stretchable in at least the vertical direction, e.g. is neither stretchable nor contractible.

After the diaper 1 of such arrangement has been put on a wearer's body, the sheet 21 is elastically stretched upwards and thereby the pleats of the suspender sheets 22A, 22B are flattened out as the cover member 2 is pulled upwards. Dimensions between the first and second folding lines 23A and 24A; 23B and 24B of the respective suspender sheets 22A, 22B in a vertical direction of the diaper 1 may be appropriately selected to ensure that stretching of the elastic sheet 21 should not be restricted.

Figure 4:
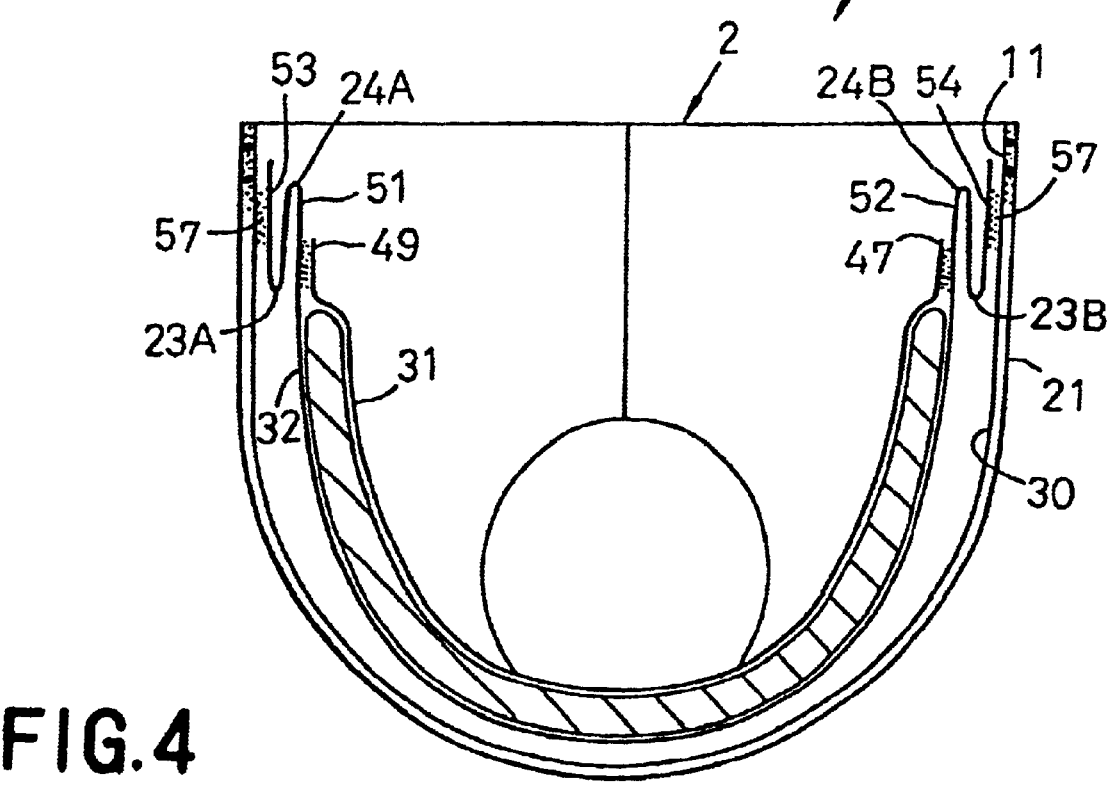
FIG. 4 is a view similar to FIG. 2 showing a specific embodiment of the invention.
Figure 5:
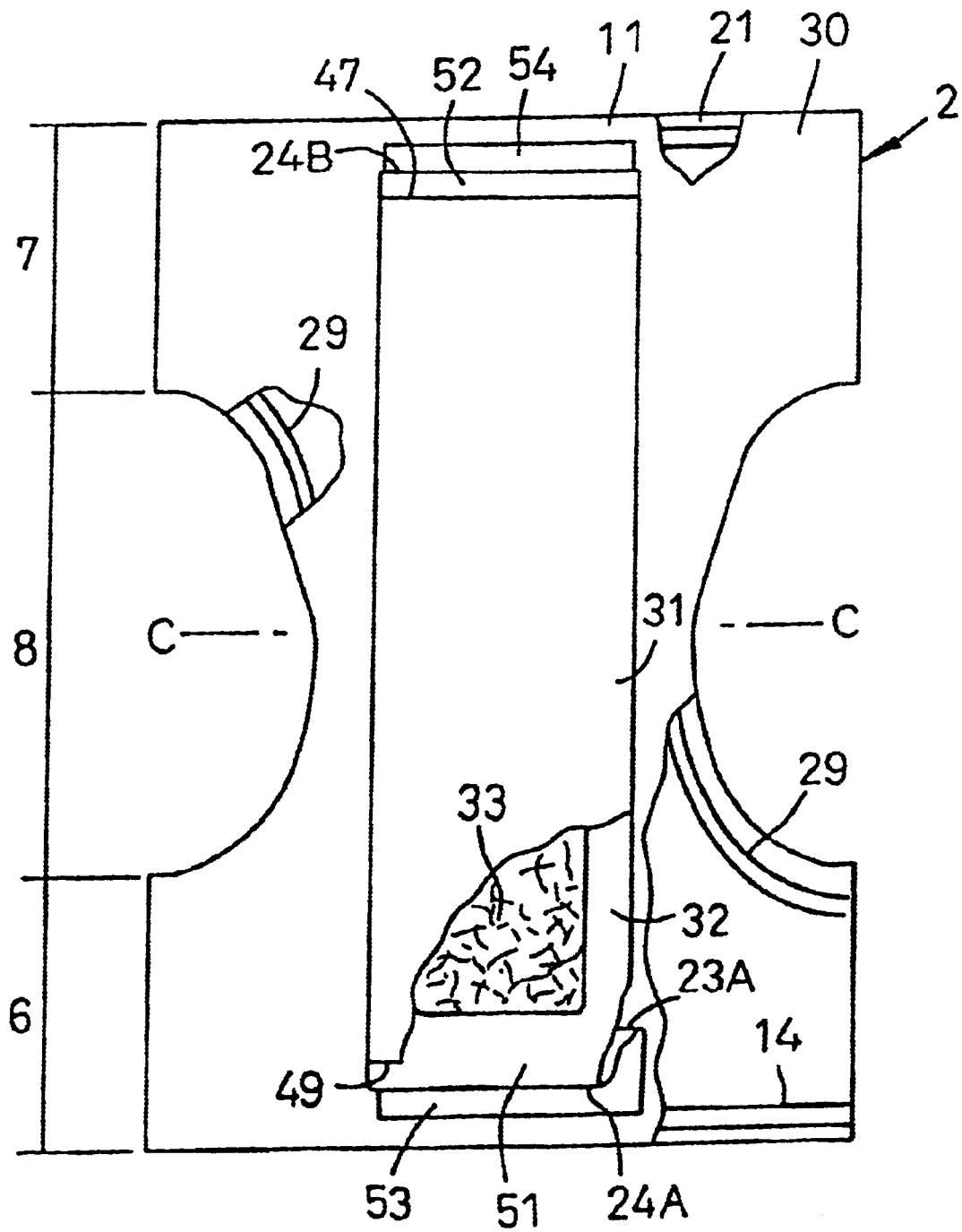
FIG. 5 is a view similar to FIG. 3 showing the specific embodiment of the invention.

FIGS. 4 and 5 are views similar to FIGS. 2 and 3, respectively, showing a specific embodiment of the invention. In this diaper 1, the cover member 2 comprises a first elastic sheet 21 and a second elastic sheet 30 placed upon the inner surface of the first elastic sheet 21. These first and second elastic sheets 21, 30 are identical in shape and size and are elastically stretchable in a vertical direction of the diaper 1. Along the peripheral edges 11 of the waist-opening 10 and the transversely opposite side edges of the crotch region 8 in the cover member 2, elastically stretchable members 14, 29 are provided. Elastically stretchable members 14, 29 extend circumferentially of a wearer's waist and legs, respectively, between the first and second sheets 21, 30, and are secured to at least one of the first and second sheets 21, 30. The first and second elastic sheets 21, 30 are bonded to each other by means of hot melt adhesive (not shown) which is intermittently distributed to avoid the chance that one of these two elastic sheets 21, 30 might restrict stretchability as well as contractibility of the other elastic sheet 21 or 30.

The top sheet 31 and the backsheet 32 of the absorbent element 3 are not elastically stretchable in a vertical direction of the diaper 1. While the topsheet 31 and the backsheet 32 are identical with each other so far as their widths are concerned, the backsheet 32 is relatively long and extends outwards beyond the longitudinally opposite ends 49, 47 of the topsheet 31 to define suspender flaps 51, 52. These suspender flaps 51, 52 are folded along first folding lines 23A, 23B lying relatively near the center line C—C of the diaper 1 and along second folding lines 24A, 24B lying relatively remote from the center line C—C so as to form pleats. Distal ends 53, 54 of the suspender flaps 51, 52 are joined to the second elastic sheet 30 in the proximity of the peripheral edges 11 of the waist-opening 10 by means of hot melt adhesive 57 (See FIG. 4).

In the case of such diaper 1, the pleats of the suspender flaps 51, 52 are flattened out as the cover member 2 is pulled upwards, so that the desired elastic stretching of the cover member 2 is not obstructed. With this diaper 1, the suspender flaps 51, 52 of the absorbent element 3 function in the same manner as the suspender sheets 22A, 22B shown in FIGS. 2 and 3. Substantially the same effect as the effect offered by the diaper 1 of FIGS. 1–3 can be achieved when a pair of non-stretchable sheets, at least in the vertical direction, are used as the suspender and these sheets are bonded to the cover member 2 as well as to the absorbent element 3.

To exploit this invention, the suspender sheets 22A, 22B may be made from a woven fabric, nonwoven fabric, a plastic sheet material or a laminate comprising some of them, all of which are not elastically stretchable at least in a vertical direction of the diaper 1. The backsheet 32 including the suspender flaps 51, 52 functioning in the same manner as the suspender sheets 22A, 22B may be made of a woven fabric, a nonwoven fabric or a plastic sheet material, all of which are also not elastically stretchable at least in the vertical direction and liquid-impervious. The liquid-pervious topsheet 31 may be made of a nonwoven fabric or an apertured plastic sheet. The first and second elastic sheets 21, 30 forming the cover member 2 may be made from a woven fabric, a nonwoven fabric, a plastic sheet material or a laminate comprising some of them, all of which are elastically stretchable at least in the vertical direction. Bonding of various members may be achieved by utilizing suitable adhesive agents such as hot melt adhesive or heat-sealing technique.

The disposable diaper according to the invention comprises a cover member having elastic stretchability in a vertical direction of the diaper and an absorbent element which is formed separately of the cover member and is not elastically stretchable at least in the vertical direction wherein these two basic components are connected to each other by the suspender sheets which are not elastically stretchable at least in the vertical direction and folded so as to form the pleats adapted to be flattened out in a vertical direction of the diaper. This unique arrangement ensures that the desired stretchability as well as contractibility of the cover member in the vertical direction should not be obstructed.

What is claimed is:

1. A disposable diaper comprising:
    a briefs-shaped cover member having a front waist region, a rear waist region and a crotch region extending between the front waist region and the rear waist region so as to define a waist-opening and a pair of leg-openings, and
    an absorbent element formed separately of said cover member, said absorbent element comprising:
        a liquid-pervious topsheet,
        a liquid-impervious backsheet, and
        a liquid-absorbent core disposed between the liquid-pervious topsheet and the liquid-impervious backsheet,
    said absorbent element longitudinally extending on an inner side of said cover member from said crotch region into said front and rear waist regions,
    said cover member being elastically stretchable in a vertical direction of said diaper,
    said absorbent element is not elastically stretchable in said vertical direction and is connected to the inner side of said cover member in proximity to the waist-opening in said front and rear waist regions by suspender sheets which are not elastically stretchable in said vertical direction, said suspender sheets being respectively formed with pleats defined by folded portions that have vertically directed openings, said pleats extending circumferentially of said front and rear waist regions and being flattenable in said vertical direction.

2. The disposable diaper according to claim 1, wherein said suspender sheets are formed separately from said cover member.

3. The disposable diaper according to claim 1, wherein said suspender sheets are formed as a part of said backsheet.

4. The disposable diaper according to claim 1, wherein said cover member comprises first and second elastic sheets which are placed one upon another and intermittently bonded.

5. The disposable diaper according to claim 1, wherein said absorbent element is provided along transversely opposite side edges thereof with elastically stretchable members.

* * * * *